US012760008B2

(12) United States Patent
Tanaka

(10) Patent No.: US 12,760,008 B2
(45) Date of Patent: Oct. 13, 2026

(54) COMPOUND, ANGIOTENSIN II TYPE 1 RECEPTOR ANTAGONIST AND PHARMACEUTICAL COMPOSITION

(71) Applicant: Alchemedicine, Inc., Tsukuba (JP)

(72) Inventor: Keigo Tanaka, Tsukuba (JP)

(73) Assignee: ALCHEMEDICINE , INC., Ibaraki (JP)

( * ) Notice: Subject to any disclaimer, the term of this patent is extended or adjusted under 35 U.S.C. 154(b) by 254 days.

(21) Appl. No.: 18/718,208

(22) PCT Filed: Dec. 27, 2022

(86) PCT No.: PCT/JP2022/048117
§ 371 (c)(1),
(2) Date: Jun. 10, 2024

(87) PCT Pub. No.: WO2023/127853
PCT Pub. Date: Jul. 6, 2023

(65) Prior Publication Data

US 2025/0051315 A1 Feb. 13, 2025

(30) Foreign Application Priority Data

Dec. 28, 2021 (JP) ................................ 2021-213587

(51) Int. Cl.

| | |
|---|---|
| ***C07D 405/14*** | (2006.01) |
| ***A61K 31/422*** | (2006.01) |
| ***A61K 31/497*** | (2006.01) |
| ***A61P 9/12*** | (2006.01) |
| ***C07D 413/14*** | (2006.01) |

(52) U.S. Cl.
CPC .......... *C07D 405/14* (2013.01); *A61K 31/422* (2013.01); *A61K 31/497* (2013.01); *A61P 9/12* (2018.01); *C07D 413/14* (2013.01)

(58) Field of Classification Search
None
See application file for complete search history.

(56) References Cited

U.S. PATENT DOCUMENTS

2002/0143024 A1 10/2002 Murugesan et al.
2014/0142149 A1 5/2014 Zhang et al.
2020/0155563 A1 5/2020 Blomgren et al.

FOREIGN PATENT DOCUMENTS

EP 0434249 A2 6/1991
JP 2003-520785 A 7/2003
JP 2012-522058 A 9/2012
WO WO 01/44239 A2 6/2001
WO WO 2005/080384 A3 9/2005
WO WO-2009158309 A2 12/2009
WO WO-2018071784 A1 4/2018
WO WO 2020/092383 A1 5/2020
WO WO-2020132594 A1 6/2020

OTHER PUBLICATIONS

International Search Report for PCT/JP2022/048117; I.A. fd Dec. 27, 2022); mailed Mar. 20, 2023 by the Japan Patent Office, Tokyo, Japan.

(Continued)

*Primary Examiner* — Samantha L Shterengarts
(74) *Attorney, Agent, or Firm* — Sterne, Kessler, Goldstein & Fox P.L.L.C.

(57) ABSTRACT

A compound represented by the following formula (1):

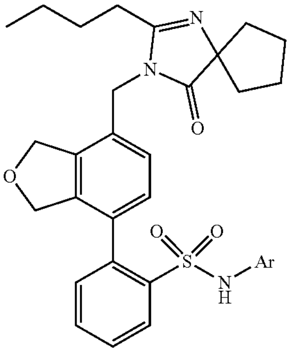

(1)

wherein

Ar is the following formula (Ar1) or (Ar2):

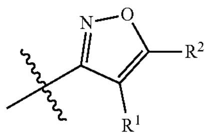

(Ar1)

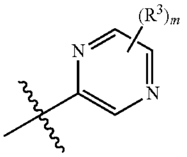

(Ar2)

wherein $R^1$ and $R^2$ are each independently an alkyl, a haloalkyl, or a halogen;

each $R^3$ is independently an alkyl, a haloalkyl, a halogen, an alkoxy, or a haloalkoxy; and m is an integer of 0 to 3, or a pharmaceutically acceptable salt thereof.

10 Claims, No Drawings

(56) References Cited

OTHER PUBLICATIONS

International Preliminary Report on Patentability (Chapter I of the Patent Cooperation Treaty), for PCT/JP2022/048117; I.A. fd Dec. 27, 2022); issued Jun. 20, 2024 by the International Bureau of WIPO, Geneva, Switzerland.

Cuspidi C, et al., "Angiotensin II receptor blockers and cardiovascular protection: focus on left ventricular hypertrophy regression and atrial fibrillation prevention." Vasc Health Risk Manag. 2008;4(1):67-73. doi: 10.2147/vhrm.2008.04.01.67, published Feb. 8, 2008.

Chen F, et al., "The effect of Sacubitril/Valsartan on cardiac function and cardiac remodeling in patients with heart failure with reduced ejection fraction." Ann Palliat Med. Aug. 2021;10(8):8684-8691. doi: 10.21037/apm-21-157.

Dickstein K, et al., OPTIMAAL Steering Committee of the OPTIMAAL Study Group. Effects of losartan and captopril on mortality and morbidity in high-risk patients after acute myocardial infarction: the OPTIMAAL randomised trial. Lancet. Sep. 7, 2002;360(9335):752-60. doi: 10.1016/s0140-6736(02)09895-1.

Brenner BM, et al., "RENAAL Study Investigators. Effects of losartan on renal and cardiovascular outcomes in patients with type 2 diabetes and nephropathy." N Engl J Med. Sep. 20, 2001;345(12):861-9. doi: 10.1056/NEJMoa011161.

Burnier M, et al., "Effect of angiotensin receptor blockers on blood pressure and renal function in patients with concomitant hypertension and chronic kidney disease: a systematic review and meta-analysis." Blood Press. Dec. 2019;28(6):358-374. doi: 10.1080/08037051.2019.1644155. Epub Aug. 8, 2019.

Cho JY, et al., "Effects of angiotensin receptor blockers on neointimal characteristics in angina patients requiring stent implantation: optical coherence tomography analysis." BMC Cardiovasc Disord. Nov. 15, 2017;17(1):278. doi: 10.1186/s12872-017-0709-9.

Wang RF, et al., "Effect of CS-088, an angiotensin AT1 receptor antagonist, on intraocular pressure in glaucomatous monkey eyes." Exp Eye Res. May 2005;80(5):629-32. doi: 10.1016/j.exer.2004.11.012. Epub Jan. 4, 2005.

Shah GB, et al., Oculohypotensive effect of angiotensin-converting enzyme inhibitors in acute and chronic models of glaucoma. J Cardiovasc Pharmacol. Aug. 2000;36(2):169-75. doi: 10.1097/00005344-200008000-00005.

Wang J, et al., "Valsartan lowers brain beta-amyloid protein levels and improves spatial learning in a mouse model of Alzheimer disease." J Clin Invest. Nov. 2007;117(11):3393-402. doi: 10.1172/JCI31547.

Kikuchi K, et al., "Clinical neuroprotective drugs for treatment and prevention of stroke." Int J Mol Sci. 2012;13(6):7739-7761. doi: 10.3390/ijms13067739. Epub Jun. 21, 2012.

Mogi M, et al., "Effects of angiotensin II receptor blockers on dementia." Hypertens Res. Sep. 2009;32(9):738-40. doi: 10.1038/hr.2009.110.

Li Y, et al., "Clinical application of angiotensin receptor blockers in patients with non-alcoholic fatty liver disease: a systematic review and meta-analysis." Oncotarget. Jan. 2, 2018;9(35):24155-24167. doi: 10.18632/oncotarget.23816.

Ejima C, et al., "A novel diet-induced murine model of steatohepatitis with fibrosis for screening and evaluation of drug candidates for nonalcoholic steatohepatitis." Physiol Rep. Nov. 2016;4(21):e13016. doi: 10.14814/phy2.13016.

Oliva S, et al., "Recent advances in potential targets for eosinophilic esophagitis treatments." Expert Rev Clin Immunol. Apr. 2020;16(4):421-428. doi: 10.1080/1744666X.2020.1742110. Epub Mar. 18, 2020.

Deng Z, et al., "Losartan protects against osteoarthritis by repressing the TGF-β1 signaling pathway via upregulation of PPARγ." J Orthop Translat. May 18, 2021;29:30-41. doi: 10.1016/j.jot.2021.03.005.

Inamadar AC. "Losartan as disease modulating therapy for recessive dystrophic epidermolysis bullosa." Dermatol Ther. Nov. 2020;33(6):e14279. doi: 10.1111/dth.14279. Epub Sep. 15, 2020.

Van Andel MM, et al., Long-term clinical outcomes of losartan in patients with Marfan syndrome: follow-up of the multicentre randomized controlled COMPARE trial. Eur Heart J. Nov. 14, 2020;41(43):4181-4187. doi: 10.1093/eurheartj/ehaa377.

Ishikane S, et al., "The role of angiotensin II in cancer metastasis: Potential of renin-angiotensin system blockade as a treatment for cancer metastasis." Biochem Pharmacol. May 2018;151:96-103. doi: 10.1016/j.bcp.2018.03.008. Epub Mar. 10, 2018.

Extended European Search Report for European Application No. 22916076.7, European Patent Office, Germany, mailed on Nov. 24, 2025, 9 pages.

COMPOUND, ANGIOTENSIN II TYPE 1 RECEPTOR ANTAGONIST AND PHARMACEUTICAL COMPOSITION

TECHNICAL FIELD

The present invention relates to a compound, an angiotensin II type 1 receptor antagonist and a pharmaceutical composition.

BACKGROUND ART

Receptors for angiotensin II include the angiotensin II type 1 receptor (AT1 receptor) and the angiotensin II type 2 receptor (AT2 receptor), and various diseases related to (mediated by) the AT1 receptor have been reported.

As AT1 receptor-related diseases, for example, hypertension (Patent Literature 1), cardiac diseases (e.g., cardiac hypertrophy, acute heart failure, chronic heart failure including congestive heart failure, diastolic failure, cardiomyopathy, angina pectoris, myocarditis, atrial fibrillation, arrhythmia, tachycardia, and myocardial infarction) (Non Patent Literatures 1 and 2), progression of heart failure after myocardial infarction (Non Patent Literature 3), renal diseases (e.g., nephritis, glomerulonephritis, glomerulosclerosis, renal failure, thrombotic microangiopathy, complications of dialysis, and organ damage including radiation-induced nephropathy) (Non Patent Literatures 4 and 5), vascular hyperplasia, occlusion, and organ damage after interventions (e.g., percutaneous transluminal coronary angioplasty, stent placement, coronary angioscopy, intravascular ultrasound, and intracoronary thrombolysis) (Non Patent Literature 6), ocular diseases (e.g., glaucoma and ocular hypertension) (Non Patent Literatures 7 and 8), neurodegenerative diseases (e.g., Alzheimer's disease) (Non Patent Literature 9), central nervous system disorders (e.g., disorders such as cerebral hemorrhage and cerebral infarction, their sequelae and complications) (Non Patent Literature 10), dementia (e.g., cerebrovascular dementia) (Non Patent Literature 11), hepatic diseases (e.g., non-alcoholic fatty liver disease) (Non Patent Literatures 12 and 13), eosinophilic esophagitis (Non Patent Literature 14), bone diseases (e.g., osteoarthritis of the knee) (Non Patent Literature 15), skin diseases (e.g., epidermolysis bullosa) (Non Patent Literature 16), systemic diseases (e.g., Marfan syndrome) (Non Patent Literature 17) and cancer (Non Patent Literature 18) have been reported.

CITATION LIST

Patent Literature

[Patent Literature 1] International Publication No. WO 2005/80384

Non Patent Literature

[Non Patent Literature 1] Vascular Health and Risk Management 2008, 4, 67.

[Non Patent Literature 2] Annals of Palliative Medicine 2021, 10, 8684.

[Non Patent Literature 3] The Lancet 2002, 360, 752.

[Non Patent Literature 4] The New England Journal of Medicine 2001, 345, 861.

[Non Patent Literature 5] Blood Pressure 2019, 28, 358.

[Non Patent Literature 6] BMC Cardiovascular Disorders 2017, 17, 278.

[Non Patent Literature 7] Experimental Eye Research 2005, 80, 629.

[Non Patent Literature 8] Journal of Cardiovascular Pharmacology 2000, 36, 169.

[Non Patent Literature 9] Journal of Clinical Investigation 2007, 117, 3393.

[Non Patent Literature 10] International Journal of Molecular Sciences 2012, 13, 7739.

[Non Patent Literature 11] Hypertension Research 2009, 32, 738.

[Non Patent Literature 12] Oncotarget 2018, 9, 24155.

[Non Patent Literature 13] Physiological Reports 2016, 4, e13016.

[Non Patent Literature 14] Expert Review of Clinical Immunology 2020, 16, 421.

[Non Patent Literature 15] Journal of Orthopaedic Translation 2021, 29, 30.

[Non Patent Literature 16] Dermatologic Therapy 2020, e14279.

[Non Patent Literature 17] European Heart Journal 2020, 41, 4181.

[Non Patent Literature 18] Biochemical Pharmacology 2018, 151, 96.

SUMMARY OF INVENTION

Technical Problem

An object of the present invention is to provide a compound having an AT1 receptor antagonistic effect, or an AT1 receptor antagonist or pharmaceutical composition containing the compound.

Solution to Problem

As a result of extensive studies, the present inventors have found that a compound having a predetermined structure has an AT1 receptor antagonistic effect, and completed the present invention.

The present invention includes the following embodiments:

[1]

A compound represented by the following formula (1):

(1)

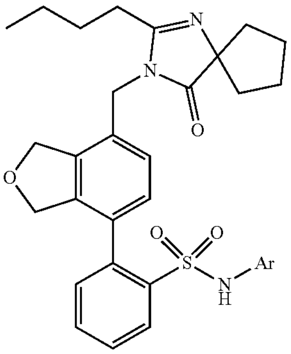

wherein

Ar is the following formula (Ar1) or (Ar2):

(Ar1)

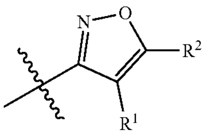

(Ar2)

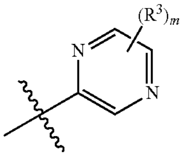

wherein $R^1$ and $R^2$ are each independently an alkyl, a haloalkyl, or a halogen;

each $R^3$ is independently an alkyl, a haloalkyl, a halogen, an alkoxy, or a haloalkoxy; and m is an integer of 0 to 3, or a pharmaceutically acceptable salt thereof.

[2]

The compound or pharmaceutically acceptable salt thereof according to [1], wherein Ar is the formula (Ar1).

[3]

The compound or pharmaceutically acceptable salt thereof according to [1] or [2], wherein $R^1$ and $R^2$ are each independently an alkyl.

[4]

The compound or pharmaceutically acceptable salt thereof according to [1], selected from the group consisting of the following compounds:

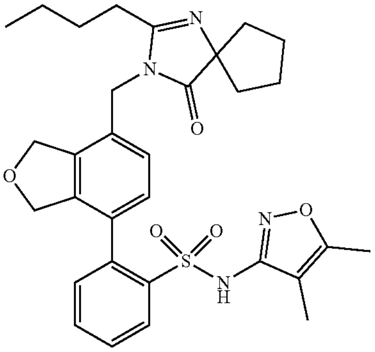

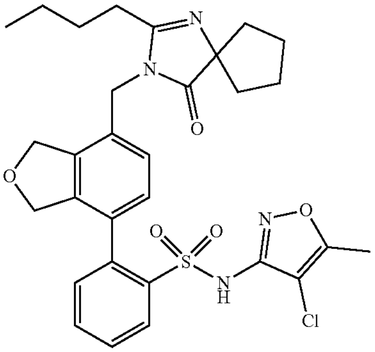

-continued

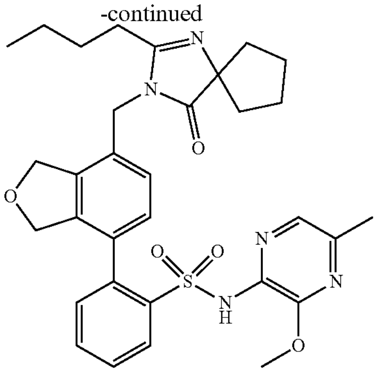

[5]

An angiotensin II type 1 receptor antagonist, comprising the compound or pharmaceutically acceptable salt thereof according to any of [1] to [4].

[6]

A pharmaceutical composition, comprising the compound or pharmaceutically acceptable salt thereof according to any of [1] to [4].

[7]

The pharmaceutical composition according to [6], for preventing or treating hypertension, cardiac diseases, progression of heart failure after myocardial infarction, renal diseases, vascular hyperplasia after interventions, occlusion after interventions, organ damage after interventions, glaucoma, ocular hypertension, Alzheimer's disease, central nervous system disorders, dementia, hepatic diseases, eosinophilic esophagitis, osteoarthritis of the knee, epidermolysis bullosa, Marfan syndrome or cancer.

[8]

The pharmaceutical composition according to [6] or [7], which is an injection, a patch, or an ophthalmic solution.

[9]

A compound represented by the following formula (2):

(2)

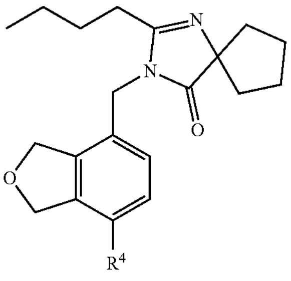

wherein $R^4$ is a leaving group, boronic acid, a boronate ester, or $—BF_3M^1$; and $M^1$ is an alkali metal, or a salt thereof.

[10]

A compound represented by the following formula (3):

(3)

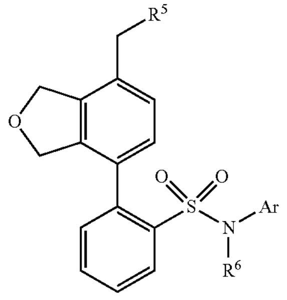

wherein

Ar is the following formula (Ar1) or (Ar2):

(Ar1)

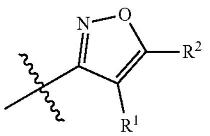

(Ar2)

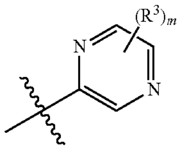

wherein $R^1$ and $R^2$ are each independently an alkyl, a haloalkyl, or a halogen;

each $R^3$ is independently an alkyl, a haloalkyl, a halogen, an alkoxy, or a haloalkoxy; and m is an integer of 0 to 3, $R^5$ is a leaving group, or —$OR^{5A}$;

$R^{5A}$ is hydrogen or a protective group; and $R^6$ is hydrogen or a protective group, or a salt thereof.

[11]

A compound represented by the following formula (4):

(4)

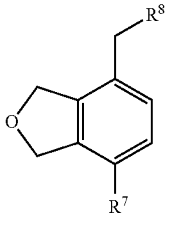

wherein $R^7$ is boronic acid, a boronate ester, or —$BF_3M^2$;

$M^2$ is an alkali metal;

$R^8$ is —$OR^{8A}$; and $R^{8A}$ is hydrogen or a protective group, or a salt thereof.

In addition, the present invention also includes the following embodiments:

[A1]

A method for inhibiting the angiotensin II type 1 receptor, comprising administering to a patient in need thereof an effective amount of the compound or pharmaceutically acceptable salt thereof according to any of [1] to [4].

[A2]

A method for preventing or treating a disease, comprising administering to a patient in need thereof an effective amount of the compound or pharmaceutically acceptable salt thereof according to any of [1] to [4].

[A3]

The method according to [A2], wherein the disease is hypertension, a cardiac disease, progression of heart failure after myocardial infarction, a renal disease, vascular hyperplasia after an intervention, occlusion after an intervention, organ damage after an intervention, glaucoma, ocular hypertension, Alzheimer's disease, a central nervous system disorder, dementia, a hepatic disease, eosinophilic esophagitis, osteoarthritis of the knee, epidermolysis bullosa, Marfan syndrome or cancer.

[B1]

The compound or pharmaceutically acceptable salt thereof according to any of [1] to [4], for use in the inhibition of the angiotensin II type 1 receptor.

[B2]

The compound or pharmaceutically acceptable salt thereof according to one of [1] to [4], for use in the prevention or treatment of a disease.

[B3]

The compound or pharmaceutically acceptable salt thereof according to [B2], wherein the disease is hypertension, a cardiac disease, progression of heart failure after myocardial infarction, a renal disease, vascular hyperplasia after an intervention, occlusion after an intervention, organ damage after an intervention, glaucoma, ocular hypertension, Alzheimer's disease, a central nervous system disorder, dementia, a hepatic disease, eosinophilic esophagitis, osteoarthritis of the knee, epidermolysis bullosa, Marfan syndrome or cancer.

[C1]

A use of the compound or pharmaceutically acceptable salt thereof according to any of [1] to [4], for the inhibition of the angiotensin II type 1 receptor.

[C2]

A use of the compound or pharmaceutically acceptable salt thereof according to any of [1] to [4], for the prevention or treatment of a disease.

[C3]

The use according to [C2], wherein the disease is hypertension, a cardiac disease, progression of heart failure after myocardial infarction, a renal disease, vascular hyperplasia after an intervention, occlusion after an intervention, organ damage after an intervention, glaucoma, ocular hypertension, Alzheimer's disease, a central nervous system disorder, dementia, a hepatic disease, eosinophilic esophagitis, osteoarthritis of the knee, epidermolysis bullosa, Marfan syndrome or cancer.

[D1]

A use of the compound or pharmaceutically acceptable salt thereof according to any of [1] to [4], in the production of an angiotensin II type 1 receptor antagonist.

[D2]

A use of the compound or pharmaceutically acceptable salt thereof according to any of [1] to [4], in the production of a pharmaceutical composition for preventing or treating a disease.

[D3]

The use according to [D2], wherein the disease is hypertension, a cardiac disease, progression of heart failure after myocardial infarction, a renal disease, vascular hyperplasia after an intervention, occlusion after an intervention, organ damage after an intervention, glaucoma, ocular hypertension, Alzheimer's disease, a central nervous system disorder, dementia, a hepatic disease, eosinophilic esophagitis, osteoarthritis of the knee, epidermolysis bullosa, Marfan syndrome or cancer.

Advantageous Effects of Invention

According to the present invention, it is possible to provide a compound having an AT1 receptor antagonistic effect, or an AT1 receptor antagonist or pharmaceutical composition containing the compound.

DESCRIPTION OF EMBODIMENTS

Embodiments of the present invention will be specifically described below, but the present invention is not limited thereto, and various modifications can be made without deviating from the gist thereof.

<Compound>

One embodiment of the present invention relates to a compound represented by the following formula (1):

(1)

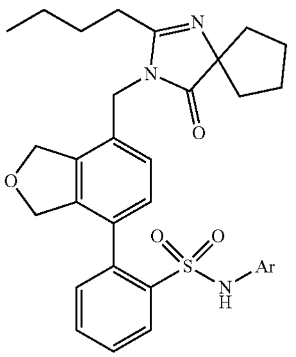

wherein

Ar is the following formula (Ar1) or (Ar2):

(Ar1)

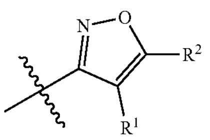

(Ar2)

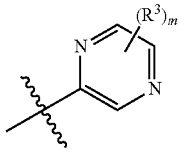

wherein $R^1$ and $R_2$ are each independently an alkyl, a haloalkyl, or a halogen;

each $R^3$ is independently an alkyl, a haloalkyl, a halogen, an alkoxy, or a haloalkoxy; and m is an integer of 0 to 3, or a pharmaceutically acceptable salt thereof.

The compound or pharmaceutically acceptable salt thereof according to the present embodiment has an AT1 receptor antagonistic effect.

In the present specification, the alkyl (including the alkyl in a haloalkyl) may be linear or branched.

In the present specification, the alkyl portion in the alkoxy (including the alkoxy in a haloalkoxy) may be linear or branched.

In formula (1), Ar is the formula (Ar1) or (Ar2), and is preferably the formula (Ar1).

In formula (1), $R^1$ is an alkyl, a haloalkyl, or a halogen, preferably an alkyl or a halogen, and more preferably an alkyl.

The alkyl (including the alkyl in a haloalkyl) of $R^1$ is preferably an alkyl having 1 to 6 carbon atoms, more preferably an alkyl having 1 to 3 carbon atoms, still more preferably an alkyl having 1 or 2 carbon atoms, and particularly preferably a methyl.

The halogen and the halo in the haloalkyl of $R^1$ are preferably fluorine, chlorine, bromine or iodine, and more preferably chlorine.

In formula (1), $R^2$ is an alkyl, a haloalkyl, or a halogen, preferably an alkyl or a halogen, and more preferably an alkyl.

The alkyl (including the alkyl in a haloalkyl) of $R^2$ is preferably an alkyl having 1 to 6 carbon atoms, more preferably an alkyl having 1 to 3 carbon atoms, still more preferably an alkyl having 1 or 2 carbon atoms, and particularly preferably a methyl.

The halogen and the halo in the haloalkyl of $R^2$ are preferably fluorine, chlorine, bromine or iodine, and more preferably chlorine.

In formula (1), each $R^3$ is independently an alkyl, a haloalkyl, a halogen, an alkoxy, or a haloalkoxy, and preferably an alkyl or an alkoxy.

The alkyl (including the alkyl in a haloalkyl) of $R^3$ is preferably an alkyl having 1 to 6 carbon atoms, more preferably an alkyl having 1 to 3 carbon atoms, still more preferably an alkyl having 1 or 2 carbon atoms, and particularly preferably a methyl.

The halogen and the halo in the haloalkyl and haloalkoxy of $R^3$ are preferably fluorine, chlorine, bromine or iodine, and more preferably chlorine.

The alkoxy (including the alkoxy in a haloalkoxy) of $R^3$ is preferably an alkoxy having 1 to 6 carbon atoms, more preferably an alkoxy having 1 to 3 carbon atoms, still more preferably an alkoxy having 1 or 2 carbon atoms, and particularly preferably a methoxy.

In formula (1), m is an integer of 0 to 3, preferably 1 or 2, and more preferably 2.

The compound represented by formula (1) is not particularly limited, but the following compounds are preferred:

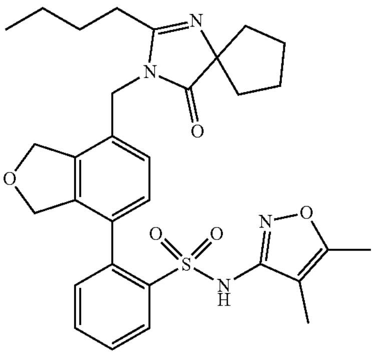

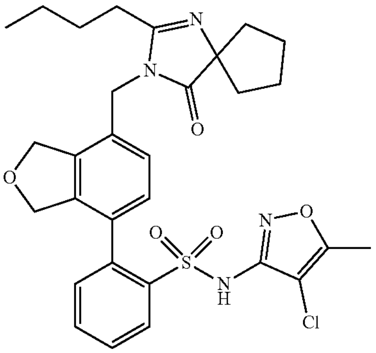

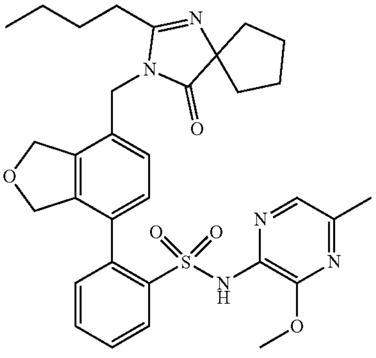

The pharmaceutically acceptable salt of the compound represented by formula (1) is not particularly limited as long as it can be used as a medicament, but examples thereof include inorganic acid salts such as hydrochlorides, sulfates, nitrates, phosphates, and hydrobromides; organic acid salts such as fumarates, maleates, malates, tartrates, succinates, citrates, methanesulfonates, p-toluenesulfonates, acetates, lactates, and palmitates; inorganic base salts such as sodium salts, potassium salts, calcium salts, magnesium salts, aluminum salts, and ammonium salts; and organic base salts such as diethylamine salts, diethanolamine salts, meglumine salts, and N,N'-dibenzylethylenediamine salts.

The compound represented by formula (1) or a pharmaceutically acceptable salt thereof may form a solvate such as a hydrate. In the present specification, the solvate is included in the compound represented by formula (1) or the pharmaceutically acceptable salts thereof.

When the compound represented by formula (1) or a pharmaceutically acceptable salt thereof has stereoisomers (e.g., enantiomers and diastereomers), the individual stereoisomers and mixtures thereof (e.g., racemates) are included in the compound represented by formula (1) or the pharmaceutically acceptable salts thereof.

<Angiotensin II Type 1 Receptor Antagonist>

One embodiment of the present invention relates to an AT1 receptor antagonist, which contains the compound represented by formula (1) or a pharmaceutically acceptable salt thereof. The AT1 receptor antagonist of the present embodiment is preferably capable of selectively inhibiting the AT1 receptor in contrast to the endothelin A receptor (ETA receptor). Selectively inhibiting the AT1 receptor allows to reduce the risk of side effects (e.g., teratogenicity) due to the inhibition of the ETA receptor.

Specifically, the ETA receptor inhibitory concentration ($IC_{50}$)/AT1 receptor inhibitory concentration ($IC_{50}$) is preferably 100 or more, more preferably 200 or more, still more preferably 500 or more, and particularly preferably 1,000 or more. The upper limit of the ETA receptor inhibitory concentration ($IC_{50}$)/AT1 receptor inhibitory concentration ($IC_{50}$) is not particularly limited, but may be, for example, 10,000, 8,000, 6,000, or 4,000. The ETA receptor inhibitory concentration and the AT1 receptor inhibitory concentration can be measured by the method described in the Examples.

The AT1 receptor inhibitory concentration ($IC_{50}$) of the AT1 receptor antagonist of the present embodiment is preferably 1.0 nM or less, more preferably 0.5 nM or less, still more preferably 0.2 nM or less, and particularly preferably 0.1 nM or less. The lower limit of the AT1 receptor inhibitory concentration ($IC_{50}$) is not particularly limited, but may be, for example, 0.0025 nM, 0.005 nM, 0.01 nM, or 0.02 nM.

The ETA receptor inhibitory concentration ($IC_{50}$) of the AT1 receptor antagonist of the present embodiment is preferably 10 nM or more, more preferably 20 nM or more, still more preferably 50 nM or more, and particularly preferably 100 nM or more. The upper limit of the ETA receptor inhibitory concentration ($IC_{50}$) is not particularly limited, but may be, for example, 1,000 nM, 800 nM, 600 nM, or 400 nM.

By using the AT1 receptor antagonist of the present embodiment, it is possible to treat and/or prevent diseases related to (mediated by) the AT1 receptor. Examples of such diseases include the diseases listed in the "Pharmaceutical Composition" section below.

The subject to which the AT1 receptor antagonist of the present embodiment or the pharmaceutical composition described below is administered is preferably a mammal, more preferably a human, monkey, cat, pig, horse, cow, mouse, rat, guinea pig, dog, and rabbit, and still more preferably a human.

<Pharmaceutical Composition>

One embodiment of the present invention relates to a pharmaceutical composition, which contains the compound represented by formula (1) or a pharmaceutically acceptable salt thereof.

Examples of the diseases to be prevented or treated by the pharmaceutical composition of the present embodiment include the following:

hypertension;

cardiac diseases (e.g., cardiac hypertrophy, acute heart failure, chronic heart failure including congestive heart failure, diastolic failure, cardiomyopathy, angina pectoris, myocarditis, atrial fibrillation, arrhythmia, tachycardia, and myocardial infarction);

progression of heart failure after myocardial infarction;

renal diseases (e.g., nephritis, glomerulonephritis, glomerulosclerosis, renal failure, thrombotic microangiopathy, complications of dialysis and organ damage including radiation-induced nephropathy);

vascular hyperplasia, occlusion, and organ damage after interventions (e.g., percutaneous transluminal coronary angioplasty, stent placement, coronary angioscopy, intravascular ultrasound, and intracoronary thrombolysis);

ocular diseases (e.g., glaucoma and ocular hypertension);

neurodegenerative diseases (e.g., Alzheimer's disease);

central nervous system disorders (e.g., disorders such as cerebral hemorrhage and cerebral infarction, their sequelae and complications);

dementia (e.g., cerebrovascular dementia);

hepatic diseases (e.g., non-alcoholic fatty liver disease);

eosinophilic esophagitis;

bone diseases (e.g., osteoarthritis of the knee);

skin diseases (e.g., epidermolysis bullosa);

systemic diseases (e.g., Marfan syndrome); and cancer.

The pharmaceutical composition of the present embodiment can be administered orally or parenterally. Examples of dosage forms for oral administration include tablets, pills, granules, powders, capsules, syrups, emulsions, and suspensions. Examples of dosage forms for parenteral administration include injections, infusions, intravenous drips, ophthalmic solutions, patches, and suppositories. Although not particularly limited, the pharmaceutical composition of the present embodiment is preferably an injection. By making it into an injection, it can be suitably used for diseases with high urgency. Examples of diseases with high urgency include acute hypertension accompanied by organ damage such as cerebral hemorrhage or myocardial infarction.

If the pharmaceutical composition of the present embodiment is an injection, the injection may contain a second active ingredient in addition to the compound represented by formula (1) or a pharmaceutically acceptable salt thereof. Examples of the second active ingredient include compounds having an AT1 receptor antagonistic effect other than the compound represented by formula (1) or pharmaceutically acceptable salts thereof, and specifically include losartan, valsartan, candesartan, telmisartan, olmesartan, irbesartan, and azilsartan.

The pharmaceutical composition of the present embodiment may contain excipients, binders, lubricants, disintegrants, sweeteners, surfactants, suspending agents, emulsifiers, coloring agents, preservatives, aromatic agents, flavoring agents, stabilizers, viscous agents, and the like, as necessary.

The dosage of the pharmaceutical composition of the present embodiment varies depending on the patient's condition and weight, the type of compound, type of disease, route of administration, and the like, and the appropriate amount can be determined by a physician.

<Intermediate Compound>

One embodiment of the present invention relates to an intermediate compound which can be used for the synthesis of the compound represented by formula (1) or a pharmaceutically acceptable salt thereof. Examples of the intermediate compound include the compounds represented by the formulae (2) to (4) below and salts thereof.

The salts of the compounds represented by formulae (2) to (4) are not particularly limited, and examples thereof include those listed as examples of the pharmaceutically acceptable salts of the compound represented by formula (1).

The compounds represented by formulae (2) to (4) or salts thereof may form a solvate such as a hydrate. In the present specification, the solvate is included in the compounds represented by formulae (2) to (4) or salts thereof.

(Intermediate Compound 1)

One embodiment of the present invention relates to a compound represented by the following formula (2):

(2)

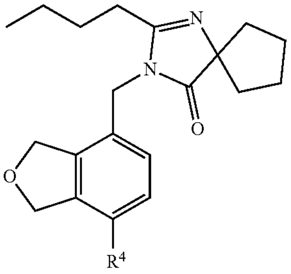

wherein $R^4$ is a leaving group, boronic acid (—$B(OH)_2$), a boronate ester, or —$BF_3M^1$; and $M^1$ is an alkali metal, or a salt thereof.

Examples of the leaving group of $R^4$ include a halogen (e.g., fluorine, chlorine, bromine, and iodine), methanesulfonyloxy, p-toluenesulfonyloxy, and trifluoromethanesulfonyloxy.

The boronate ester of $R^4$ can be represented, for example, by —$B(OR^{4A})_2$. Examples of $R^{4A}$ include an alkyl (e.g., an alkyl having 1 to 6 carbon atoms or an alkyl having 1 to 3 carbon atoms).

The two $R^{4A}$s of —$B(OR^{4A})_2$ may form, together with the oxygen and boron to which they are bound directly or indirectly, a 5- or 6-membered heterocyclic ring. The heterocyclic ring may have a substituent. Examples of the substituent of the heterocyclic ring include an alkyl (e.g., an alkyl having 1 to 3 carbon atoms), a cycloalkyl (e.g., a cycloalkyl having 5 or 6 carbon atoms), and an aryl (e.g., phenyl). Examples of —$B(OR^{4A})_2$ include groups having the following structure:

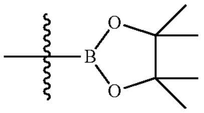 [SMILES: *B1OC(C)(C)C(C)(C)O1]

Examples of the alkyl metal of $M^1$ include lithium, sodium, and potassium.

(Intermediate Compound 2)

One embodiment of the present invention relates to a compound represented by the following formula (3):

(3)

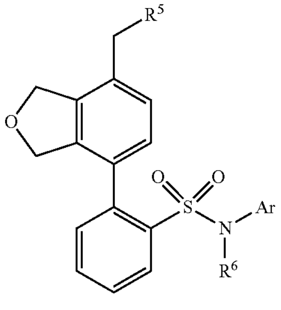

wherein

Ar is the following formula (Ar1) or (Ar2):

(Ar1)

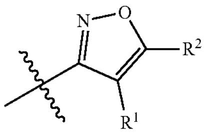

(Ar2)

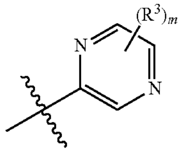

wherein $R^1$ and $R^2$ are each independently an alkyl, a haloalkyl, or a halogen;

each $R^3$ is independently an alkyl, a haloalkyl, a halogen, an alkoxy, or a haloalkoxy; and m is an integer of 0 to 3, $R^5$ is a leaving group, or —$OR^{5A}$;

$R^{5A}$ is hydrogen or a protective group; and $R^6$ is hydrogen or a protective group, or a salt thereof.

In formula (3), the preferred form of Ar is as described in the <Compound> section above.

Examples of the leaving group of $R^5$ include a halogen (e.g., fluorine, chlorine, bromine, and iodine), methanesulfonyloxy, p-toluenesulfonyloxy, and trifluoromethanesulfonyloxy.

The protective group of $R^{5A}$ is not particularly limited as long as it is a protective group of hydroxyl groups, and examples thereof include methoxymethyl (MOM), tert-butyldimethylsilyl (TBS), benzyl (Bn), benzoyl (Bz), acetyl (Ac), trimethylsilyl (TMS), and triethylsilyl (TES).

The protective group of $R^6$ is not particularly limited as long as it is a protective group of amino groups, and examples thereof include methoxymethyl (MOM), tert-butoxycarbonyl (Boc), benzyloxycarbonyl (Cbz), 9-fluorenylmethyloxycarbonyl group (Fmoc), and allyloxycarbonyl group (Alloc).

(Intermediate Compound 3)

One embodiment of the present invention relates to a compound represented by the following formula (4):

(4)

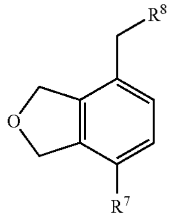

wherein $R^7$ is boronic acid (—$B(OH)_2$), a boronate ester, or —$BF_3M^2$;

$M^2$ is an alkali metal;

$R^8$ is —$OR^{8A}$; and $R^{8A}$ is hydrogen or a protective group, or a salt thereof.

The boronate ester of $R^7$ can be represented, for example, by —$B(OR^{7A})_2$. Examples of $R^{7A}$ include an alkyl (e.g., an alkyl having 1 to 6 carbon atoms or an alkyl having 1 to 3 carbon atoms).

The two $R^{7A}$s of —$B(OR^{7A})_2$ may form, together with the oxygen and boron to which they are bound directly or indirectly, a 5- or 6-membered heterocyclic ring. The heterocyclic ring may have a substituent. Examples of the substituent of the heterocyclic ring include an alkyl (e.g., an alkyl having 1 to 3 carbon atoms), a cycloalkyl (e.g., a cycloalkyl having 5 or 6 carbon atoms), and an aryl (e.g., phenyl). Examples of —$B(OR^{7A})_2$ include groups having the following structure:

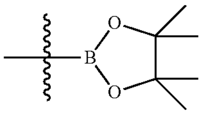 [SMILES: *B1OC(C)(C)C(C)(C)O1]

Examples of the alkyl metal of $M^2$ include lithium, sodium, and potassium.

The protective group of $R^{8A}$ is not particularly limited as long as it is a protective group of hydroxyl groups, and examples thereof include methoxymethyl (MOM), tert-butyldimethylsilyl (TBS), benzyl (Bn), benzoyl (Bz), acetyl (Ac), trimethylsilyl (TMS), and triethylsilyl (TES).

<Method for Producing Compound>

The compound represented by formula (1) or a pharmaceutically acceptable salt thereof can be synthesized by using a method known in the art as appropriate. An example of the synthesis method includes the following scheme A:

<Scheme A>

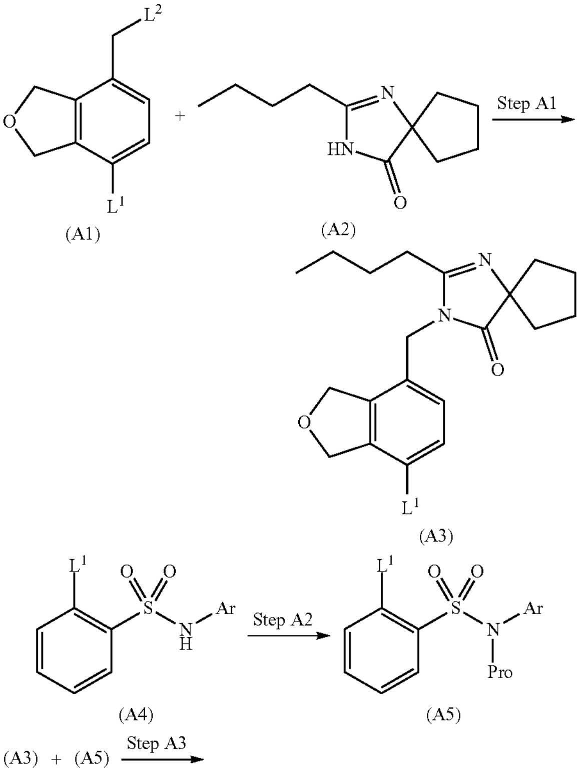

-continued

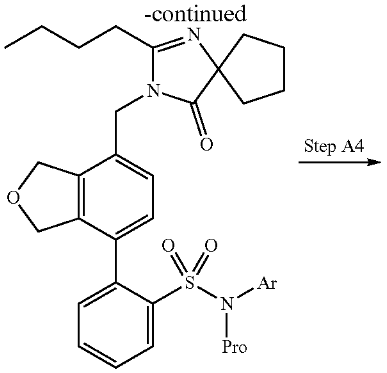

(A6)

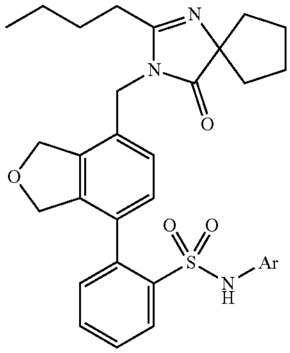

(A7)

In Scheme A, Ar is as described above, Li to L3 are leaving groups and the like, and Pro is a protective group.

In Scheme A, the compound (A2) is reacted with a metal hydride (e.g. sodium hydride) and then reacted with the compound (A1) to obtain the compound (A3) (Step A1). The amino group of the compound (A4) is protected with a protective group (e.g., methoxymethyl group) to obtain the compound (A5) (Step A2). The compound (A3) is reacted with the compound (A5) to obtain the compound (A6) (Step A3), and the compound (A6) is deprotected to obtain the compound (A7) (Step A4).

The method for synthesizing the compound represented by formula (1) or pharmaceutically acceptable salts thereof is not limited to the above Scheme A, and the appropriate synthetic route and reaction conditions can be appropriately set by those skilled in the art according to the structure of the final compound.

EXAMPLES

Hereinafter, the present invention will be described in more details using examples, but the technical scope of the present invention is not limited thereto.

Production Example 1-1

7-Bromo-1,3-dihydroisobenzofuran-4-amine hydrochloride

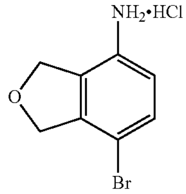

A hydrogen chloride, 1,4-dioxane solution (4 mol/L, 15.0 mL) was slowly added to a mixture of tert-butyl (7-bromo-1,3-dihydroisobenzofuran-4-yl) carbamate (4.90 g, 15.6 mmol) and dichloromethane (50.0 mL) at 0° C. and stirred at room temperature for 6 hours. The solvent of the reaction mixture was distilled off under reduced pressure, and the residue was washed with diethyl ether to obtain the title compound (2.90 g).

$^1$H NMR (400 MHZ, DMSO-d$_6$) δ 7.29 (d, J=8.0 Hz, 1H), 6.78 (d, J=8.0 Hz, 1H), 5.05 (bs, 2H), 4.89 (bs, 2H).

Production Example 1-2

4,7-Dibromo-1,3-dihydroisobenzofuran

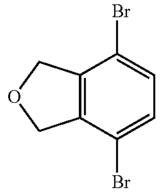 [SMILES: Brc1ccc(Br)c2c1COC2]

Under argon atmosphere, a mixture of copper (II) bromide (3.03 g, 13.5 mmol), tert-butyl nitrite (1.54 g, 14.9 mmol), and acetonitrile (20.0 mL) was slowly added to a mixture of 7-bromo-1,3-dihydroisobenzofuran-4-amine hydrochloride (2.90 g, 11.64 mmol) and acetonitrile (40.0 m L) at 0° C. and stirred at 80° C. for 6 hours. The reaction mixture was brought to room temperature, then ice-cold water was added, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (1.70 g).

1H NMR (400 MHZ, DMSO-d6) δ 7.45 (bs, 1H), 5.09 (s, 4H).

Production Example 1-3

7-Bromo-1,3-dihydroisobenzofuran-4-carbaldehyde

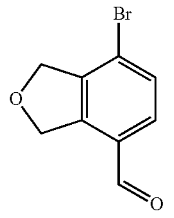 [SMILES: O=Cc1ccc(Br)c2c1COC2]

Under argon atmosphere, n-butyl lithium (2.3 M hexane solution, 5.65 mL, 7.34 mmol) was slowly added to a mixture of 4,7-dibromo-1,3-dihydroisobenzofuran (1.70 g, 6.12 mmol) and diethyl ether (20.0 mL) at −78° C. and stirred at the same temperature for 1 hour. N,N-dimethylformamide (0.95 mL, 12.2 mmol) was slowly added to the reaction mixture and stirred at −78° C. for 30 minutes. A saturated aqueous ammonium chloride solution was added to the reaction mixture, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (0.80 g).

1H NMR (400 MHZ, DMSO-d6) δ 10.03 (s, 1H), 7.87-7.79 (m, 2H), 5.37 (s, 2H), 5.01 (s, 2H).

Production Example 1-4

(7-Bromo-1,3-dihydroisobenzofuran-4-yl)methanol

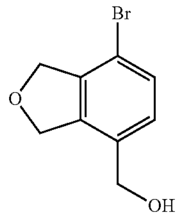 [SMILES: OCc1ccc(Br)c2c1COC2]

Sodium borohydride (379 mg, 10.6 mmol) was added to a mixture of 7-bromo-1,3-dihydroisobenzofuran-4-carbaldehyde (800 mg, 3.52 mmol) and methanol (10 mL) at 0° C. and the reaction mixture was stirred at room temperature for 1 hour. Ice-cold water was added to the reaction mixture, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (0.75 g).

1H NMR (400 MHZ, DMSO-d6) δ 7.44 (d, J=8.0 Hz, 1H), 7.20 (d, J=8.0 Hz, 1H), 5.26 (t, J=5.6 Hz, 1H), 5.14 (s, 2H), 4.96 (s, 2H), 4.42 (d, J=5.6 Hz, 2H).

Production Example 1-5

4-Bromo-7-(chloromethyl)-1,3-dihydroisobenzofuran

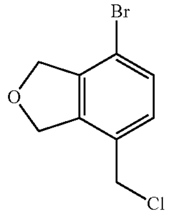 [SMILES: ClCc1ccc(Br)c2c1COC2]

Thionyl chloride (584 mg, 4.91 mmol) was slowly added to a mixture of (7-bromo-1,3-dihydroisobenzofuran-4-yl)methanol (750 mg, 3.27 mmol) and dichloromethane (15 mL) at 0° C. and stirred at the same temperature for 30 minutes. A small amount of N,N-dimethylformamide was added to the reaction mixture and stirred at the same temperature for 2 hours. Ice-cold water was added to the reaction mixture, followed by extraction with dichloromethane. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (0.63 g).

1H NMR (400 MHZ, DMSO-d6) δ 7.50 (d, J=8.0 Hz, 1H), 7.30 (d, J=8.0 Hz, 1H), 5.22 (s, 2H), 5.00 (s, 2H), 4.73 (s, 2H).

Production Example 1-6

3-((7-Bromo-1,3-dihydroisobenzofuran-4-yl)methyl)-2-butyl-1,3-diazaspiro[4,4]nona-1-en-4-one

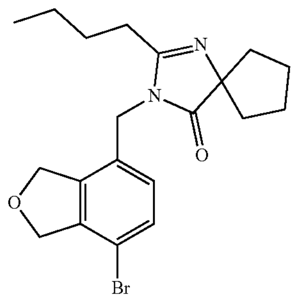 [SMILES: CCCCC1=NC2(CCCC2)C(=O)N1Cc1ccc(Br)c2c1COC2]

50% sodium hydride (153 mg, 6.36 mmol) was slowly added to a mixture of 2-butyl-1,3-diazaspiro[4,4]nona-1-en-4-one (494 mg, 2.55 mmol) and DMF (10 mL) at 0° C. and stirred at the same temperature for 30 minutes. A mixture of 4-bromo-7-(chloromethyl)-1,3-dihydroisobenzofuran (630 mg, 2.55 mmol) and DMF (5 mL) was slowly added to the reaction mixture and stirred at the same temperature for 2 hours. Ice-cold water was added to the reaction mixture, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (0.90 g).

ESI-MS: m/z 405.10 [M+1]+, 407.12 [M+3]+

Production Example 1-7

2-Butyl-3-((7-(4,4,5,5-tetramethyl-1,3,2-dioxaborolan-2-yl)-1,3-dihydroisobenzofuran-4-yl)methyl)-1,3-diazaspiro[4,4]nona-1-en-4-one

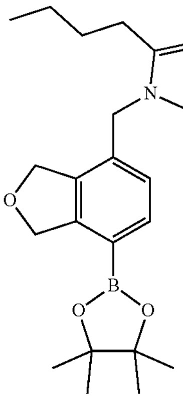

Under argon atmosphere, [1,1'-bis(diphenylphosphino)ferrocene]palladium (II) dichloride dichloromethane adduct (50.3 mg, 0.0617 mmol) was added to a mixture of 3-((7-bromo-1,3-dihydroisobenzofuran-4-yl)methyl)-2-butyl-1,3-diazaspiro[4,4]nona-1-en-4-one (500 mg, 1.23 mmol), bis(pinacolato)diboron (471 mg, 1.85 mmol), potassium acetate (245 mg, 2.47 mmol), and 1,4-dioxane (10 mL), and the reaction mixture was stirred at 100° C. for 16 hours. The reaction mixture was brought to room temperature, then water was added, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (0.35 g).

ESI-MS: m/z 453.26 [M+1]+.

Production Example 1-8

2-Bromo-N-(4,5-dimethylisoxazol-3-yl)benzenesulfonamide

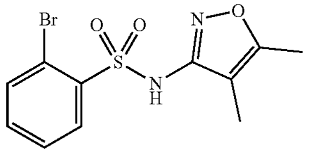 [SMILES: Cc1onc(NS(=O)(=O)c2ccccc2Br)c1C]

4-Dimethylaminopyridine (54.5 mg, 0.446 mmol) and 2-bromobenzenesulfonyl chloride (1.71 g, 6.69 mmol) were slowly added to a mixture of 4,5-dimethylisoxazol-3-amine (500 mg, 4.46 mmol) and pyridine (10.0 mL) at 0° C., and the reaction mixture was stirred at 50° C. for 16 hours. The reaction mixture was brought to room temperature, then ice-cold water was added, followed by extraction with ethyl acetate. The organic layer was washed with 2 mol/L hydrochloric acid and a saturated sodium chloride solution, and dried over sodium sulfate. The solvent was distilled off under reduced pressure to obtain the title compound (1.20 g) as a crude product. The obtained crude product was used in the next reaction without further purification.

ESI-MS: m/z 330.91 [M+1]+, 332.93 [M+3]+

Production Example 1-9

2-Bromo-N-(4,5-dimethylisoxazol-3-yl)-N-(methoxymethyl)benzenesulfonamide

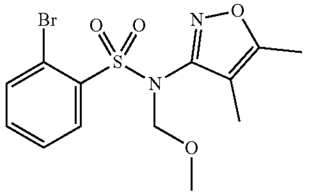 [SMILES: COCN(c1noc(C)c1C)S(=O)(=O)c1ccccc1Br]

50% sodium hydride (217 mg, 4.53 mmol) was slowly added to a mixture of crude 2-bromo-N-(4,5-dimethylisoxazol-3-yl)benzenesulfonamide (1.20 g, 3.62 mmol) and DMF (20.0 mL) at 0° C. and stirred at the same temperature for 30 minutes. Chloromethyl methyl ether (583 mg, 7.25 mmol) was slowly added to the reaction mixture and stirred at room temperature for 3 hours. Ice-cold water was added to the reaction mixture, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (0.90 g).

1H NMR (400 MHZ, CDCl3) δ 8.02-8.00 (m, 1H), 7.76-7.74 (m, 1H), 7.40-7.38 (m, 2H), 5.24 (s, 2H), 3.54 (s, 3H), 2.30 (s, 3H), 1.99 (s, 3H).

Production Example 1-10

2-(7-((2-Butyl-4-oxo-1,3-diazaspiro[4,4]nona-1-en-3-yl)methyl)-1,3-dihydroisobenzofuran-4-yl)-N-(4,5-dimethylisoxazol-3-yl)-N-(methoxymethyl)benzenesulfonamide

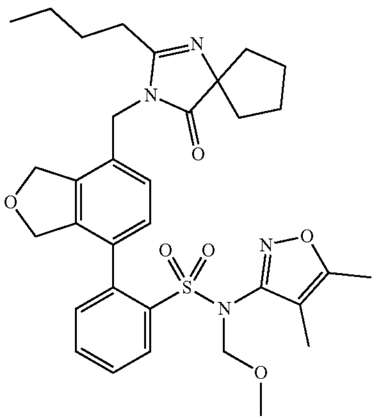 [SMILES: CCCCC1=NC2(CCCC2)C(=O)N1Cc1ccc(-c2ccccc2S(=O)(=O)N(COC)c2noc(C)c2C)c2c1COC2]

Under argon atmosphere, [1,1'-bis(diphenylphosphino)ferrocene]palladium (II) dichloride dichloromethane adduct (63 mg, 0.07 mmol) was added to a mixture of 2-bromo-N-(4,5-dimethylisoxazol-3-yl)-N-(methoxymethyl)benzenesulfonamide (347 mg, 0.92 mmol), 2-butyl-3-((7-(4,4,5,5-tetramethyl-1,3,2-dioxaborolan-2-yl)-1,3-dihydroisobenzofuran-4-yl)methyl)-1,3-diazaspiro[4,4]nona-1-en-4-one (350 mg, 0.77 mmol), 1,4-dioxane (5.0 mL), water (0.5 mL), and potassium carbonate (314 mg, 1.54 mmol), and the reaction mixture was stirred at 100° C. for 16 hours. The reaction mixture was brought to room temperature, then water was added, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (0.25 g).

ESI-MS: m/z 621.31 [M+1]+

Example 1

2-(7-((2-Butyl-4-oxo-1,3-diazaspiro[4,4]nona-1-en-3-yl)methyl)-1,3-dihydroisobenzofuran-4-yl)-N-(4,5-dimethylisoxazol-3-yl)benzenesulfonamide

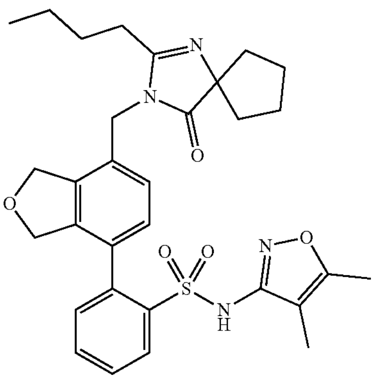 [SMILES: CCCCC1=NC2(CCCC2)C(=O)N1Cc1ccc(-c2ccccc2S(=O)(=O)Nc2noc(C)c2C)c2c1COC2]

6 mol/L hydrochloric acid (1.5 mL) was added to a mixture of 2-(7-(2-butyl-4-oxo-1,3-diazaspiro[4,4]nona-1-en-3-yl)methyl)-1,3-dihydroisobenzofuran-4-yl)-N-(4,5-dimethylisoxazol-3-yl)-N-(methoxymethyl)benzenesulfonamide (250 mg, 0.40 mmol) and methanol (3 mL) at 0° C., and the reaction mixture was stirred at 50° C. for 16 hours. The reaction mixture was brought to room temperature, then ice-cold water was added, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (55 mg).

ESI-MS: m/z 577.30 [M+1]+

1H NMR (400 MHZ, DMSO-d6) δ 10.51 (s, 1H), 8.06 (dd, J=7.6, 1.6 Hz, 1H), 7.67-7.60 (m, 2H), 7.26 (d, J=7.2 Hz, 1H), 7.00 (d, J=8.0 Hz, 1H), 6.89 (d, J=7.6 Hz, 1H), 4.99-4.97 (m, 2H), 4.73-4.67 (m, 3H), 4.50-4.47 (m, 1H), 2.34 (t, J=7.6 Hz, 2H), 2.19 (s, 3H), 1.89-1.84 (m, 6H), 1.71-1.69 (m, 2H), 1.63 (s, 3H), 1.55-1.48 (m, 2H), 1.33-1.23 (m, 3H), 0.82 (t, J=7.2 Hz, 3H).

Production Example 1-11

4-Bromo-7-((tetrahydro-2H-pyran-2-yl)oxy)methyl)-1,3-dihydroisobenzofuran

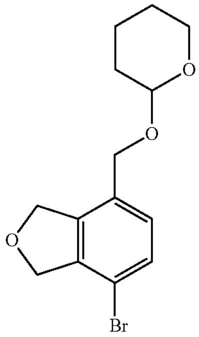 [SMILES: Brc1ccc(COC2CCCCO2)c2c1COC2]

3,4-Hydro-2H-pyran (2.1 g, 26.2 mmol) and a small amount of p-toluenesulfonic acid were slowly added to a mixture of (7-bromo-1,3-dihydroisobenzofuran-4-yl)methanol (3.0 g, 13.1 mmol) and dichloromethane (30 mL) at 0° C. and stirred at room temperature for 3 hours. Ice-cold water was added to the reaction mixture, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (2.9 g).

1H NMR (400 MHZ, DMSO): δ 7.38 (d, J=8.0 Hz, 1H), 7.13 (d, J=8.4 Hz, 1H), 5.27 (d, J=1.6 Hz, 2H), 5.11 (t, J=4.0 Hz, 2H), 4.69 (t, J=8.0 Hz, 2H), 4.42 (d, J=12.4 Hz, 1H), 3.90-3.85 (m, 1H), 3.59-3.54 (m, 1H), 1.88-1.84 (m, 1H), 1.79-1.73 (m, 1H), 1.68-1.57 (m, 4H).

Production Example 1-12

4,4,5,5-Tetramethyl-2-(7-((tetrahydro-2H-pyran-2-yl)oxy)methyl)-1,3-dihydroisobenzofuran-4-yl)-1,3,2-dioxaborolane

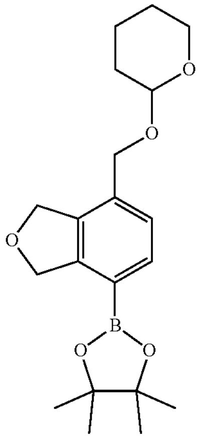 [SMILES: CC1(C)OB(c2ccc(COC3CCCCO3)c3c2COC3)OC1(C)C]

Under argon atmosphere, [1,1'-bis(diphenylphosphino)ferrocene]palladium (II) dichloride dichloromethane adduct (130 mg, 0.159 mmol) was added to a mixture of 4-bromo-7-((tetrahydro-2H-pyran-2-yl)oxy)methyl)-1,3-dihydroisobenzofuran (1.0 g, 3.19 mmol), bis(pinacolato)diboron (969 mg, 3.38 mmol), potassium acetate (937 mg, 9.57 mmol), and 1,4-dioxane (10 mL), and the reaction mixture was stirred at 100° C. for 16 hours. The reaction mixture was brought to room temperature, then ice-cold water was added, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (300 mg).

1H NMR (400 MHZ, DMSO): δ 7.38 (d, J=8.0 Hz, 1H), 7.13 (d, J=8.4 Hz, 1H), 5.07-5.02 (m, 4H), 4.64 (t, J=8.0 Hz, 2H), 4.42 (d, J=12.4 Hz, 1H), 3.77-3.72 (m, 1H), 3.49-3.45 (m, 1H), 1.67-1.64 (m, 2H), 1.52-1.56 (m, 4H), 1.28 (s, 12H).

Production Example 1-13

N-(4,5-Dimethylisoxazol-3-yl)-N-(methoxymethyl)-2-(7-((tetrahydro-2H-pyran-2-yl)oxy)methyl)-1,3-dihydroisobenzofuran-4-yl)benzenesulfonamide

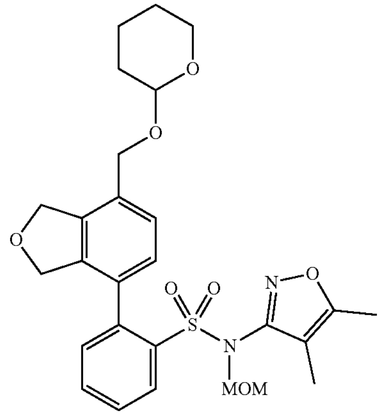

Under argon atmosphere, [1,1'-bis(diphenylphosphino)ferrocene]palladium (II) dichloride dichloromethane adduct (135 mg, 0.166 mmol) was added to a mixture of 4,4,5,5-tetramethyl-2-(7-((tetrahydro-2H-pyran-2-yl)oxy)methyl)-1,3-dihydroisobenzofuran-4-yl)-1,3,2-dioxaborolane (600 mg, 1.66 mmol), 2-bromo-N-(4,5-dimethylisoxazol-3-yl)-N-(methoxymethyl)benzenesulfonamide (749 mg, 1.99 mmol), 1,4-dioxane (7.0 mL), water (0.5 mL), and potassium carbonate (687 mg, 4.98 mmol), and the reaction mixture was stirred at 100° C. for 16 hours. The reaction mixture was brought to room temperature, then ice-cold water was added, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (400 mg).

1H NMR (400 MHZ, DMSO): δ 7.97 (d, J=8.0 Hz, 1H), 7.70 (t, J=14.8 Hz, 1H), 7.58 (t, J=15.6 Hz, 1H), 7.37 (d, J=7.2 Hz, 1H), 7.30 (d, J=7.6 Hz, 1H), 7.16 (d, J=7.6 Hz, 1H), 5.15 (s, 2H), 4.84-4.78 (m, 2H), 4.75-4.67 (m, 2H), 4.51-4.47 (m, 1H), 4.31-4.23 (m, 2H), 3.80-3.76 (m, 1H), 3.50-3.47 (m, 1H), 3.19 (s, 3H), 2.31 (s, 3H), 1.81 (s, 3H), 1.68-1.65 (m, 2H), 1.51-1.48 (m, 4H).

Production Example 1-14

N-(4,5-Dimethylisoxazol-3-yl)-2-(7-(hydroxymethyl)-1,3-dihydroisobenzofuran-4-yl)-N-(methoxymethyl)benzenesulfonamide

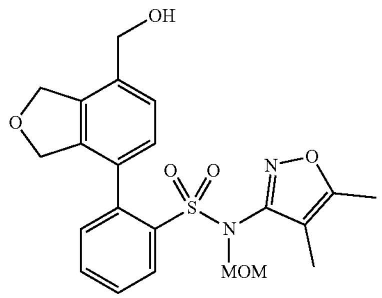

p-Toluenesulfonic acid (35.2 mg, 0.189 mmol) was added to a mixture of N-(4,5-dimethylisoxazol-3-yl)-N-(methoxymethyl)-2-(7-((tetrahydro-2H-pyran-2-yl)oxy)methyl)-1,3-dihydroisobenzofuran-4-yl)benzenesulfonamide (500 mg, 0.946 mmol) and methanol (8.0 mL) at 0° C. and stirred at room temperature for 3 hours. Water was added to the reaction mixture, followed by extraction with dichloromethane. The organic layer was washed with a saturated sodium bicarbonate solution and a saturated sodium chloride solution, dried over sodium sulfate, and the solvent was distilled off under reduced pressure. The residue was purified by silica gel column chromatography (hexane/ethyl acetate) to obtain the title compound (300 mg).

1H NMR (400 MHZ, CDCl3): δ 7.97 (d, J=8.0 Hz, 1H), 7.70 (t, J=14.8 Hz, 1H), 7.58 (t, J=15.6 Hz, 1H), 7.37 (d, J=7.2 Hz, 1H), 7.30 (d, J=7.6 Hz, 1H), 7.16 (d, J=7.6 Hz, 1H), 5.28-5.25 (m, 1H), 5.13-5.06 (m, 2H), 4.82-4.72 (m, 2H), 4.53-4.51 (m, 2H), 4.33-4.23 (m, 2H), 3.19 (s, 3H), 2.31 (s, 3H), 1.81 (s, 3H).

Production Example 1-15

2-(7-(Bromomethyl)-1,3-dihydroisobenzofuran-4-yl)-N-(4,5-dimethylisoxazol-3-yl)-N-(methoxymethyl)benzenesulfonamide

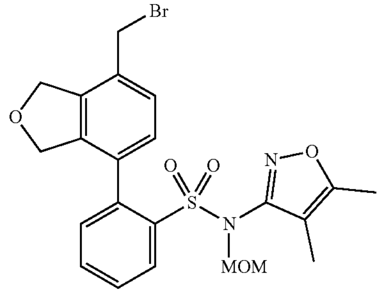

Tetrabromomethane (290 mg, 0.877 mmol) was added to N-(4,5-dimethylisoxazol-3-yl)-2-(7-(hydroxymethyl)-1,3-dihydroisobenzofuran-4-yl)-N-(methoxymethyl)benzenesulfonamide (300 mg, 0.675 mmol) and dichloromethane (7.0 mL) solution at 0° C., then after 10 minutes, triphenylphosphine (176 mg, 0.675 mmol) was added at the same temperature. The reaction mixture was heated to room temperature and stirred for 2 hours. Ice-cold water was added to the reaction mixture, followed by extraction with dichloromethane. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (250 mg).

1H NMR (400 MHZ, CDCl3): δ 7.97 (d, J=8.0 Hz, 1H), 7.70 (t, J=14.8 Hz, 1H), 7.58 (t, J=15.6 Hz, 1H), 7.41-7.39 (m, 2H), 7.16 (d, J=7.6 Hz, 1H), 5.19-5.14 (m, 2H), 4.81-4.74 (m, 4H), 4.33-4.21 (m, 2H), 3.19 (s, 3H), 2.31 (s, 3H), 1.81 (s, 3H).

Production Example 1-16

2-(7-((2-Butyl-4-oxo-1,3-diazaspiro[4,4]nona-1-en-3-yl)methyl)-1,3-dihydroisobenzofuran-4-yl)-N-(4,5-dimethylisoxazol-3-yl)-N-(methoxymethyl)benzenesulfonamide

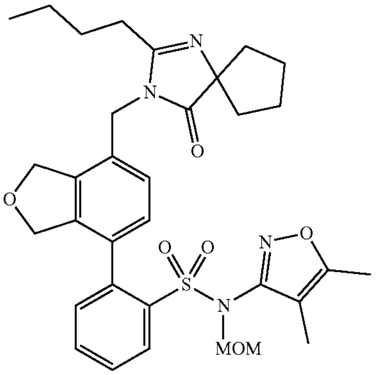

60% sodium hydride (31.5 mg, 0.788 mmol) was slowly added to a DMF (2.0 mL) solution of 2-butyl-1,3-diazaspiro[4,4]nona-1-en-4-one (108 mg, 0.473 mmol) at 0° C. and stirred at room temperature for 30 minutes. A mixture of 2-(7-(bromomethyl)-1,3-dihydroisobenzofuran-4-yl)-N-(4,5-dimethylisoxazol-3-yl)-N-(methoxymethyl)benzenesulfonamide (200 mg, 0.394 mmol) and DMF (1.0 mL) was slowly added to the reaction mixture and stirred at room temperature for 2 hours. Ice-cold water was added to the reaction mixture, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (80 mg).

1H NMR (400 MHZ, DMSO): 7.97 (d, J=8.0 Hz, 1H), 7.70 (t, J=14.8 Hz, 1H), 7.58 (t, J=15.6 Hz, 1H), 7.37 (d, J=7.2 Hz, 1H), 7.30 (d, J=7.6 Hz, 1H), 6.98 (d, J=7.6 Hz, 1H), 5.02 (s, 2H), 4.80-4.69 (m, 4H), 4.30-4.21 (m, 2H), 3.18 (s, 3H), 2.30 (s, 4H), 1.85-1.80 (m, 9H), 1.70-1.68 (m, 2H), 1.53-1.49 (m, 2H), 1.31-1.23 (m, 3H), 0.84-0.81 (m, 3H).

Production Example 2-1

2-Bromo-N-(3-methoxy-5-methylpyrazin-2-yl)benzenesulfonamide

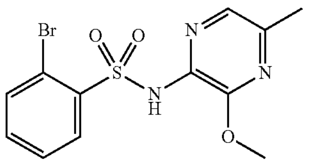 [SMILES: COc1nc(C)cnc1NS(=O)(=O)c1ccccc1Br]

4-Dimethylaminopyridine (128 mg, 1.05 mmol) and 2-bromobenzenesulfonyl chloride (1.1 g, 4.3 mmol) were added to a mixture of 3-methoxy-5-methylpyrazin-2-amine (500 mg, 3.5 mmol) and pyridine (5.0 mL) at room temperature, and the reaction mixture was stirred at 50° C. for 12 hours. The reaction mixture was brought to room temperature, then 2 mol/L hydrochloric acid (5.0 mL) was added, followed by extraction with ethyl acetate. The organic layer was washed with a saturated sodium chloride solution, and dried over sodium sulfate. The solvent was distilled off under reduced pressure to obtain the title compound (1.20 g) as a crude product. The obtained crude product was purified by silica gel column chromatography (hexane/ethyl acetate) to obtain the title compound (1.0 g).

1H NMR (400 MHZ, DMSO-d6): δ 10.99 (s, 1H), 8.07 (d, J=6.8 Hz, 1H), 7.80 (dd, J=0.8 Hz, 1H), 7.59-7.51 (m, 3H), 3.86 (s, 3H), 2.26 (s, 3H).

Production Example 2-2

2-Bromo-N-(3-methoxy-5-methylpyrazin-2-yl)-N-((2-(trimethylsilyl) ethoxy)methyl)benzenesulfonamide

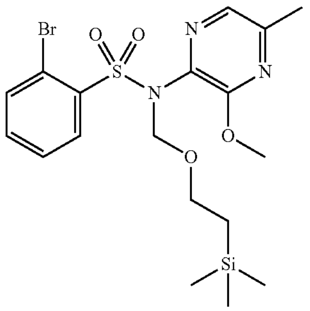 [SMILES: COc1nc(C)cnc1N(COCC[Si](C)(C)C)S(=O)(=O)c1ccccc1Br]

Potassium carbonate (380 mg, 2.79 mmol) was added to a mixture of 2-bromo-N-(3-methoxy-5-methylpyrazin-2-yl)benzenesulfonamide (500 mg, 1.39 mmol) and DMF (5.0 mL) at 0° C. and stirred at the same temperature for 30 minutes. 2-(Trimethylsilyl) ethoxymethyl chloride (350 mg, 2.08 mmol) was slowly added to the reaction mixture at 0° C. and stirred at room temperature for 1 hour. Ice-cold water was added to the reaction mixture, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (500 mg).

1H NMR (400 MHZ, DMSO-d6): δ 8.09-8.07 (m, 1H), 7.99 (s, 1H), 7.87-7.85 (m, 1H), 7.57-7.54 (m, 2H), 5.14 (s, 2H), 3.78 (s, 3H), 3.62-3.58 (m, 2H), 2.42 (s, 3H), 0.76-0.72 (m, 2H), 0.065 (s, 9H).

Production Example 2-3

2-(7-((2-Butyl-4-oxo-1,3-diazaspiro[4,4]nona-1-en-3-yl)methyl)-1,3-dihydroisobenzofuran-4-yl)-N-(3-methoxy-5-methylpyrazin-2-yl)-N-((2-(trimethylsilyl) ethoxy)methyl)benzenesulfonamide

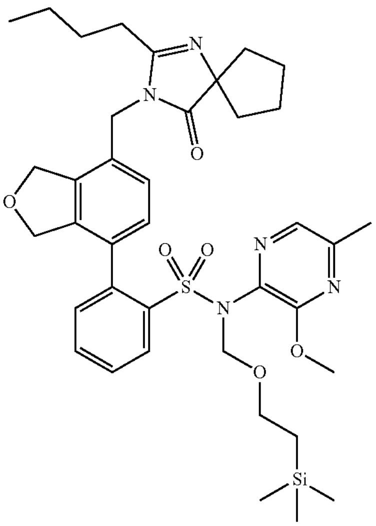 [SMILES: CCCCC1=NC2(CCCC2)C(=O)N1Cc1ccc(-c2ccccc2S(=O)(=O)N(COCC[Si](C)(C)C)c2ncc(C)nc2OC)c2c1COC2]

Under argon atmosphere, [1,1'-bis(diphenylphosphino) ferrocene]palladium (II) dichloride dichloromethane adduct (67 mg, 0.09 mmol) was added to a mixture of 2-bromo-N-(3-methoxy-5-methylpyrazin-2-yl)-N-((2-(trimethylsilyl) ethoxy)methyl)benzenesulfonamide (400 mg, 0.78 mmol), 2-butyl-3-((7-(4,4,5,5-tetramethyl-1,3,2-dioxaborolan-2-yl)-1,3-dihydroisobenzofuran-4-yl)methyl)-1,3-diazaspiro [4,4]nona-1-en-4-one (445 mg, 0.98 mmol), 1,4-dioxane (4.5 mL), water (0.5 mL), and potassium carbonate (340 mg, 2.71 mmol), and the reaction mixture was stirred at 100° C. for 12 hours. The reaction mixture was brought to room temperature, then water was added, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (170 mg).

1H NMR (400 MHZ, DMSO-d6): δ 8.15 (d, J=7.6 Hz, 1H), 7.796 (s, 1H), 7.69-7.58 (m, 2H), 7.32 (d, J=7.2 Hz, 1H), 7.11 (d, J=8 Hz, 1H), 6.91 (d, J=7.6 Hz, 1H), 4.99 (s, 2H), 4.74-4.67 (m, 6H), 3.76 (s, 3H), 3.45 (t, J=8 Hz, 2H), 2.42 (s, 3H), 2.28 (t, J=7.2 Hz, 2H), 1.86-183 (m, 6H), 1.69 (s, 2H), 1.49-1.47 (m, 2H), 1.28-1.23 (m, 4H), 0.81 (m, 3H), 0.095 (s, 9H).

Example 2

2-(7-((2-Butyl-4-oxo-1,3-diazaspiro[4,4]nona-1-en-3-yl)methyl)-1,3-dihydroisobenzofuran-4-yl)-N-(3-methoxy-5-methylpyrazin-2-yl)benzenesulfonamide

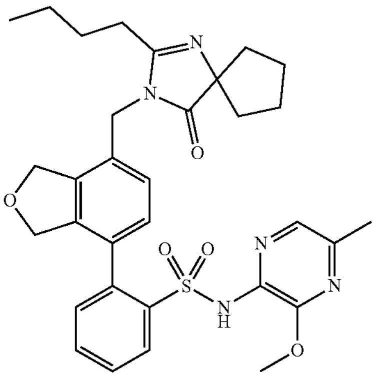 [SMILES: CCCCC1=NC2(CCCC2)C(=O)N1Cc1ccc(-c2ccccc2S(=O)(=O)Nc2ncc(C)nc2OC)c2c1COC2]

50% sulfuric acid (2.0 mL) was added to a mixture of 2-(7-((2-butyl-4-oxo-1,3-diazaspiro[4,4]nona-1-en-3-yl) methyl)-1,3-dihydroisobenzofuran-4-yl)-N-(3-methoxy-5-methylpyrazin-2-yl)-N-((2-(trimethylsilyl) ethoxy)methyl) benzenesulfonamide (170 mg, 0.231 mmol) and methanol (2 mL) at 0° C., and the reaction mixture was stirred at 0° C. for 10 hours. The reaction mixture was concentrated under reduced pressure, and to the obtained residue was added ice-cold water and a saturated sodium bicarbonate solution to bring the pH to neutral, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (38 mg).

ESI-MS: m/z 604.67 [M+1]+1H NMR (400 MHZ, DMSO-d6): δ 11.67 (s, 1H), 10.04 (s, 1H), 8.06 (d, J=6.8 Hz, 1H), 7.60-7.52 (m, 3H), 7.26-6.90 (m, 2H), 6.78-6.78 (m, 1H), 4.96 (s, 1H), 4.77-4.68 (m, 2H), 4.58-4.44 (m, 2H), 3.82-3.79 (m, 3H), 2.32-2.26 (m, 5H), 1.86 (s, 6H), 1.69 (s, 2H), 1.49-1.47 (m, 2H), 1.26-1.25 (m, 2H), 0.79 (s, 3H).

Production Example 3-1

2-Bromo-N-(4-chloro-5-methylisoxazol-3-yl)benzenesulfonamide

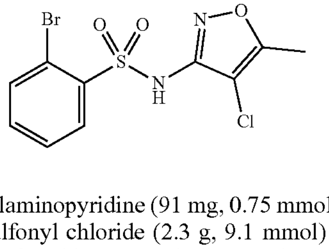

4-Dimethylaminopyridine (91 mg, 0.75 mmol) and 2-bromobenzenesulfonyl chloride (2.3 g, 9.1 mmol) were added to a mixture of 4-chloro-5-methylisoxazol-3-amine (1.0 g, 7.6 mmol) and pyridine (5.0 mL) at room temperature, and the reaction mixture was stirred at 80° C. for 6 hours. The reaction mixture was brought to room temperature, then ice-cold water was added, followed by extraction with ethyl acetate. The organic layer was washed with a saturated sodium chloride solution, dried over sodium sulfate, and the solvent was distilled off under reduced pressure. The obtained crude product was purified by silica gel column chromatography (hexane/ethyl acetate) to obtain the title compound (850 mg).

1H NMR (400 MHZ, DMSO-d6): δ 11.68 (s, 1H), 8.00 (dd, J=2 Hz, 1H), 7.92 (dd, J=1.6 Hz 1H), 7.63-7.59 (m, 2H), 3.34 (s, 3H).

Production Example 3-2

2-Bromo-N-(4-chloro-5-methylisoxazol-3-yl)-N-(methoxymethyl)benzenesulfonamide

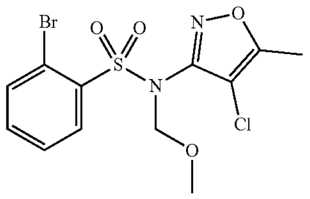

60% sodium hydride (194 mg, 4.87 mmol) was slowly added to a mixture of 2-bromo-N-(4-chloro-5-methylisoxazol-3-yl)benzenesulfonamide (850 mg, 2.42 mmol) and DMF (5.0 mL) at 0° C. and stirred at the same temperature for 30 minutes. Chloromethyl methyl ether (292 mg, 3.63 mmol) was slowly added to the reaction mixture and stirred at room temperature for 1 hour. Ice-cold water was added to the reaction mixture, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (800 mg).

1H NMR (400 MHZ, DMSO-d6): δ 8.01 (dd, J=2 Hz, 1H), 7.92 (dd, J=1.6 Hz, 1H), 7.63-7.59 (m, 2H), 5.19 (s, 2H), 3.38 (s, 3H), 2.42 (s, 3H).

Production Example 3-3

2-(7-((2-Butyl-4-oxo-1,3-diazaspiro[4,4]nona-1-en-3-yl)methyl)-1,3-dihydroisobenzofuran-4-yl)-N-(4-chloro-5-methylisoxazol-3-yl)-N-(methoxymethyl) benzenesulfonamide

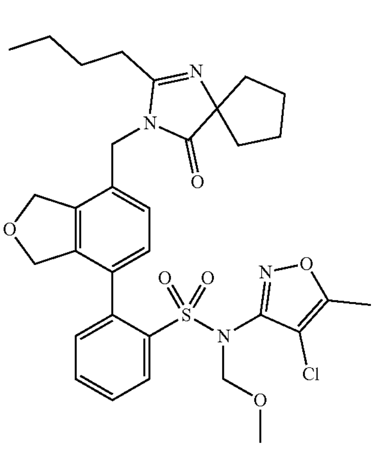

Under argon atmosphere, [1,1'-bis(diphenylphosphino) ferrocene]palladium (II) dichloride dichloromethane adduct (82.5 mg, 0.10 mmol) was added to a mixture of 2-bromo-N-(4-chloro-5-methylisoxazol-3-yl)-N-(methoxymethyl) benzenesulfonamide (400 mg, 1.01 mmol), 2-butyl-3-((7-(4,4,5,5-tetramethyl-1,3,2-dioxaborolan-2-yl)-1,3-dihydroisobenzofuran-4-yl)methyl)-1,3-diazaspiro[4,4] nona-1-en-4-one (549 mg, 1.21 mmol), 1,4-dioxane (4.5 mL), water (0.5 mL), and potassium carbonate (419 mg, 3.03 mmol), and the reaction mixture was stirred at 100° C. for 12 hours. The reaction mixture was brought to room temperature, then water was added, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (150 mg).

1H NMR (400 MHZ, DMSO-d6): δ 8.00 (d, J=8 Hz, 1H), 7.74 (t, J=7.6 Hz, 1H), 7.64 (t, J=7.6 Hz, 1H), 7.38 (d, J=7.6 Hz, 1H), 7.15 (d, J=7.6 Hz, 1H), 6.98 (d, J=8 Hz, 1H), 5.02 (s, 2H), 4.76-4.70 (m, 4H), 4.45-4.34 (m, 2H), 3.22 (s, 3H), 2.41 (s, 3H), 2.32-2.28 (m, 2H), 1.85-1.83 (m, 6H), 1.70-1.68 (m, 2H), 1.53-1.49 (m, 2H), 1.31-1.23 (m, 2H), 0.83 (t, J=7.6 Hz, 3H).

Example 3

2-(7-((2-Butyl-4-oxo-1,3-diazaspiro[4,4]nona-1-en-3-yl)methyl)-1,3-dihydroisobenzofuran-4-yl)-N-(4-chloro-5-methylisoxazol-3-yl)benzenesulfonamide

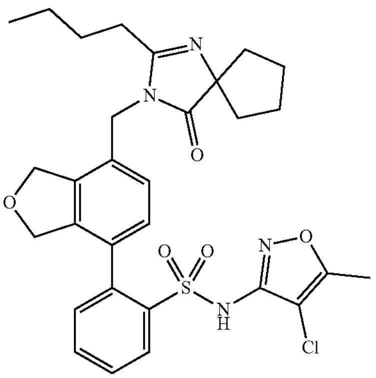 [SMILES: CCCCC1=NC2(CCCC2)C(=O)N1Cc1ccc(-c2ccccc2S(=O)(=O)Nc2noc(C)c2Cl)c2c1COC2]

50% sulfuric acid (2.0 mL) was slowly added to a mixture of 2-(7-((2-butyl-4-oxo-1,3-diazaspiro[4,4]nona-1-en-3-yl) methyl)-1,3-dihydroisobenzofuran-4-yl)-N-(4-chloro-5-methylisoxazol-3-yl)-N-(methoxymethyl)benzenesulfonamide (150 mg, 0.23 mmol) and methanol (2 mL) at 0° C., and the reaction mixture was stirred at 50° C. for 2 hours. The reaction mixture was concentrated under reduced pressure, and to the obtained residue was added ice-cold water and a saturated sodium bicarbonate solution to bring the pH to neutral, followed by extraction with ethyl acetate. The organic layer was washed with a saturated sodium chloride solution, dried over sodium sulfate, and the solvent was distilled off under reduced pressure. The residue was purified by silica gel column chromatography (hexane/ethyl acetate) to obtain the title compound (48 mg).

ESI-MS: m/z 597.67 [M+1]+

1H NMR (400 MHZ, DMSO-d6): δ 11.17 (s, 1H), 7.97 (t, J=3.6 Hz, 1H), 7.39 (bs, 2H), 7.09 (d, J=7.6 Hz, 1H), 7.03 (s, 1H), 6.81 (d, J=8 Hz, 1H), 4.91 (s, 2H), 4.63 (s, 2H), 4.52 (s, 2H), 2.36-2.32 (m, 2H), 2.12 (s, 3H), 1.88-1.83 (m, 6H), 1.70-1.68 (m, 2H), 1.55-1.48 (m, 2H), 1.33-1.23 (m, 2H), 0.83 (t, J=7.6 Hz, 3H).

Test Example 1: Angiotensin II Type 1 Receptor Inhibitory Effect

The inhibitory effect on angiotensin II type 1 receptor was studied by the following method.

CHO-K1-mt aequorin-Gα16 cells forced to express human angiotensin II type 1 receptor (Accession Number: NP 000676.1) were cultured in an antibiotic-free medium for 18 hours and then treated with PBS-EDTA (5 mM EDTA). After centrifugation (2 minutes, 405×g, room temperature), the cells were suspended in assay buffer (DMEM/HAM's F12 with HEPES+0.1% BSA protease free).

$1\times10^6$ cells/mL of the cells were incubated at room temperature for 4 hours or more in the presence of Coelenterazin h (Molecular Probes) at a final concentration of 5 μM to confirm the agonist response by angiotensin II, and determine the concentration of angiotensin II corresponding to EC 80.

Then, 50 μL of the cell suspension treated with Coelenterazin h at 10,000 cells/well and 50 μL of assay buffer containing the test substance (final concentration: 0.5% DMSO) were added to a 96-well plate. After 15 minutes, 100 μL of angiotensin II solution was added so that the final concentration reached the EC80 concentration, and the receptor activity was measured by the amount of luminescence using FDSS6000 (Hamamatsu Photonics). IC50 values were calculated using XLfit (IDBS).

An IC50 value of 1.0 nM or less, or an inhibitory effect of 50% or more exhibited at 1.0 nM was designated as "A", an IC50 value greater than 100 nM, or an inhibitory effect smaller than 50% exhibited at 100 nM was designated as "C", and those between "A" and "C" were designated as "B". The results are shown in Table 1.

TABLE 1

| AT1 Receptor Inhibitory Effect | |
|---|---|
| Example 1 | A |
| Example 2 | B |
| Example 3 | B |

Test Example 2: Endothelin a Receptor Inhibitory Effect

The inhibitory effect on endothelin A receptor was studied by the following method.

CHO-K1-mt aequorin cells forced to express human endothelin A receptor (Accession Number: NP_001948.1) were cultured in an antibiotic-free medium for 18 hours and then treated with PBS-EDTA (5 mM EDTA). After centrifugation (2 minutes, 405×g, room temperature), the cells were suspended in assay buffer (DMEM/HAM'S F12 with HEPES+0.1% BSA protease free). $1\times10^6$ cells/mL of the cells were incubated at room temperature for 4 hours in the presence of Coelenterazin h (Molecular Probes) at a final concentration of 5 μM to confirm the agonist response by endothelin, and determine the concentration of endothelin corresponding to EC 80.

Then, 50 μL of the cell suspension treated with Coelenterazin h at 10,000 cells/well and 50 μL of assay buffer containing the test substance (final concentration: 0.5% DMSO) were added to a 96-well plate. After 15 minutes, endothelin was added so that the final concentration reached the EC80 concentration, and the receptor activity was measured by the amount of luminescence using FDSS6000 (Hamamatsu Photonics). IC50 values were calculated using XLfit (IDBS).

An IC50 value of 1.0 nM or less, or an inhibitory effect of 50% or more exhibited at 1.0 nM was designated as "A", an IC50 value greater than 100 nM, or an inhibitory effect smaller than 50% exhibited at 100 nM was designated as "C", and those between "A" and "C" were designated as "B". The results are shown in Table 2.

TABLE 2

| ETA Receptor Inhibitory Effect | |
|---|---|
| Example 1 | C |
| Example 2 | B |
| Example 3 | B |

Test Example 3: Suppressive Effect on Angiotensin II-Induced Hypertensive Activity Male Wistar rats aged 8 to 12 weeks underwent catheterization of the trachea for airway management, catheterization of the carotid artery for blood pressure measurement, and catheterization of the femoral vein for angiotensin II (ATII) administration, under analgesic treatment and urethane anesthesia. After confirming that blood pressure and heart rate had stabilized, 1 mg/kg (15 mL/kg) of solvent (PBS) or test substance (the compound of Example 1) adjusted with the solvent was administered intravenously over 10 minutes. Then, ATII (300 ng/kg) was administered intravenously and blood pressure was monitored until 10 minutes after administration. The test was performed with n=3 in each group. For analysis, using 2 minutes before ATII administration as a pre-value, the systolic and diastolic blood pressures at the pre-value and 20 seconds immediately after ATII administration, when the blood pressure is maximum, were determined and the differences (delta values) from the pre-values were calculated. Student's t-test was used to compare the delta values between the solvent administration group and test substance administration group.

TABLE 3

| Suppressive Effect on Angiotensin II-Induced Hypertensive Activity | | |
|---|---|---|
| | Solvent | Example 1 |
| Systolic Blood Pressure | 73 ± 13 | 8 ± 3 * |
| Diastolic Blood Pressure | 56 ± 7 | 9 ± 5 * |

What is claimed is:

1. A compound represented by the following formula (1):

(1)

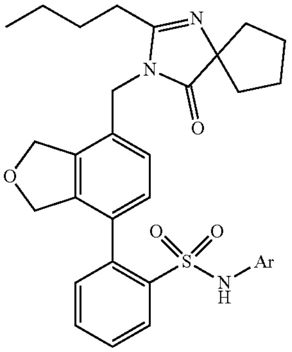

wherein

Ar is the following formula (Ar1) or (Ar2):

(Ar1)

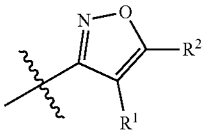

(Ar2)

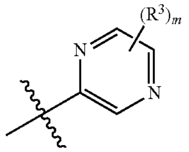

wherein $R^1$ and $R^2$ are each independently an alkyl, a haloalkyl, or a halogen;

each $R^3$ is independently an alkyl, a haloalkyl, a halogen, an alkoxy, or a haloalkoxy; and m is an integer of 0 to 3, or a pharmaceutically acceptable salt thereof.

2. The compound or pharmaceutically acceptable salt thereof according to claim 1, wherein Ar is the formula (Ar1).

3. The compound or pharmaceutically acceptable salt thereof according to claim 1, wherein $R^1$ and $R^2$ are each independently an alkyl.

4. The compound or pharmaceutically acceptable salt thereof according to claim 1, selected from the group consisting of the following compounds:

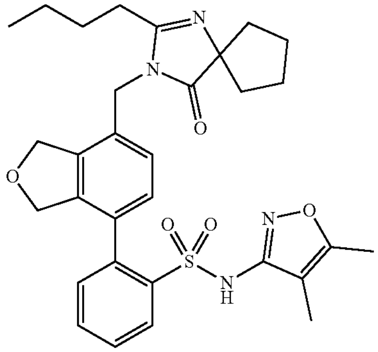

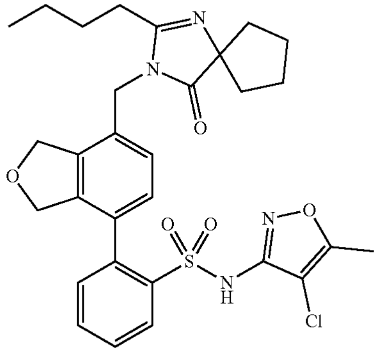

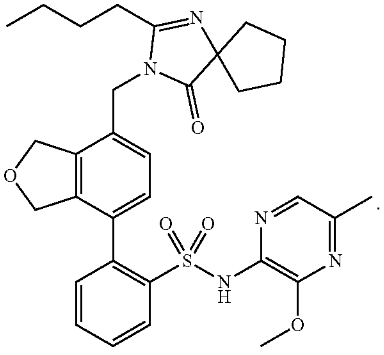

5. A method for inhibiting an angiotensin II type 1 receptor, comprising administering to a patient in need thereof an effective amount of the compound represented by the following formula (1), (1)

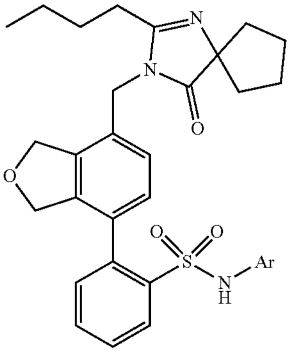

wherein

Ar is the following formula (Ar1) or (Ar2):

(Ar1)

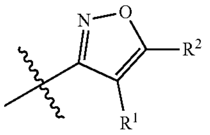

(Ar2)

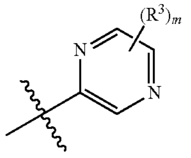

wherein $R^1$ and $R^2$ are each independently an alkyl, a haloalkyl, or a halogen;

each $R^3$ is independently an alkyl, a haloalkyl, a halogen, an alkoxy, or a haloalkoxy; and m is an integer of 0 to 3, or a pharmaceutically acceptable salt thereof.

6. A pharmaceutical composition, comprising the compound or pharmaceutically acceptable salt thereof according to claim 1.

7. A method for treating hypertension, cardiac diseases, progression of heart failure after myocardial infarction, renal diseases, vascular hyperplasia after interventions, occlusion after interventions, organ damage after interventions, glaucoma, ocular hypertension, Alzheimer's disease, central nervous system disorders, dementia, hepatic diseases, eosinophilic esophagitis, osteoarthritis of the knee, epidermolysis bullosa or Marfan syndrome, comprising administering to a patient in need thereof an effective amount of a compound represented by the following formula (1), or pharmaceutically acceptable salt thereof, (1)

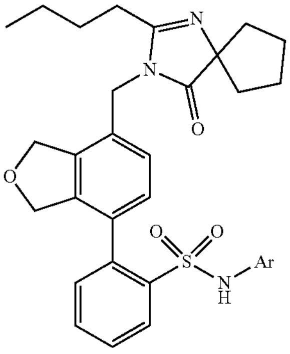

wherein

Ar is the following formula (Ar1) or (Ar2):

(Ar1)

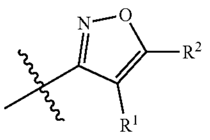

-continued (Ar2)

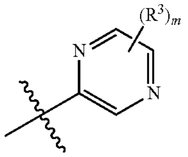

wherein $R^1$ and $R^2$ are each independently an alkyl, a haloalkyl, or a halogen;

each $R^3$ is independently an alkyl, a haloalkyl, a halogen, an alkoxy, or a haloalkoxy; and m is an integer of 0 to 3, or a pharmaceutically acceptable salt thereof.

8. The pharmaceutical composition according to claim 6, which is an injection, a patch, or an ophthalmic solution.

9. A compound represented by the following formula (2):

(2)

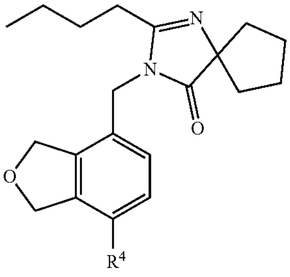

wherein $R^4$ is a leaving group, boronic acid, a boronate ester, or $—BF_3M^1$; and $M^1$ is an alkali metal, or a salt thereof.

10. A compound represented by the following formula (3):

(3)

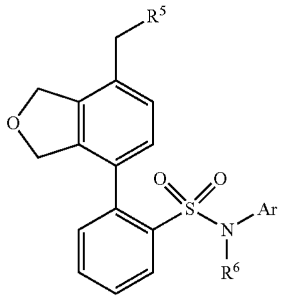

wherein

Ar is the following formula (Ar1) or (Ar2):

(Ar1)

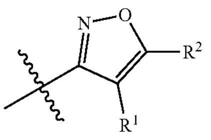

-continued
(Ar2)
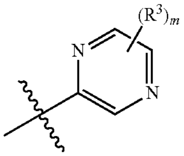
wherein
$R^1$ and $R^2$ are each independently an alkyl, a haloalkyl, or a halogen;
each $R^3$ is independently an alkyl, a haloalkyl, a halogen, an alkoxy, or a haloalkoxy; and
m is an integer of 0 to 3,
$R^5$ is a leaving group, or —$OR^{5A}$;
$R^{5A}$ is hydrogen or a protective group; and
$R^6$ is hydrogen or a protective group,
or a salt thereof.
* * * * *